United States Patent [19]

Takematsu et al.

[11] Patent Number: 5,223,016
[45] Date of Patent: Jun. 29, 1993

[54] HERBICIDAL COMPOSITIONS COMPRISING BENZOFURYLOXYPHENYLUREA OR BENZOPYRANYLOXYPHENYLUREA HERBICIDES AND DICAMBA, TRICLOPYR, MECOPROP, FLUROXYPYR, BENTAZONE, OR METRIBUZIN

[75] Inventors: Tetsuo Takematsu; Hitoshi Kuramochi; Takashi Sato, all of Utsunomiya, Japan

[73] Assignee: Mitsui Petrochemical Industries, Ltd., Tokyo, Japan

[21] Appl. No.: 679,067

[22] PCT Filed: Oct. 12, 1990

[86] PCT No.: PCT/JP90/01317
§ 371 Date: Jun. 6, 1991
§ 102(e) Date: Jun. 6, 1991

[87] PCT Pub. No.: WO91/05474
PCT Pub. Date: May 2, 1991

[30] Foreign Application Priority Data

Oct. 16, 1989 [JP] Japan ................ 1-266104
Jan. 20, 1990 [JP] Japan ................ 2-9501

[51] Int. Cl.$^5$ ............ A01N 43/16; A01N 37/10; A01N 39/02; A01N 43/707
[52] U.S. Cl. ............................ 504/130; 504/134; 504/140; 504/132; 504/139; 504/138
[58] Field of Search ............ 71/115, 88, 91, 93, 71/94, 116

[56] References Cited

U.S. PATENT DOCUMENTS 4,838,924 6/1989 Takematsu et al. ............ 71/88

FOREIGN PATENT DOCUMENTS 0275556  7/1988  European Pat. Off.
55-594309 11/1979 Japan.
59-65003  4/1984  Japan.
62138404 12/1985  Japan.
63-201180 8/1988  Japan.

Primary Examiner—Allen J. Robinson
Assistant Examiner—S. Mark Clardy
Attorney, Agent, or Firm—Sherman & Shalloway

[57] ABSTRACT

Combinations of (A) N,N-di-substituted urea of formula (I) and a compound selected from (B) 3,6-dichloro-2-methoxybenzoic acid, [(3,5,6-trichloro-2-pyridyl)-oxy]acetic acid triethylamine salt, 2-(4-chloro-2-methylphenoxy)propionic acid, 4-amino-3,5-dichloro-6-fluoro-2-pyridineoxy acetic acid, 3-isopropyl-1H-2,1,3-benzothiazin-4(3H)-one-2,2-dioxide and 4-amino-6-(1,1-dimethylethyl)-3-(methylthio)1,2,4-triazin-5(4H)-one. These combinations exhibit herbicidal activity against a wide range of weeds even in a comparatively small dosage, and are safe and show no phytotoxicity to useful crops.

12 Claims, No Drawings

HERBICIDAL COMPOSITIONS COMPRISING BENZOFURYLOXYPHENYLUREA OR BENZOPYRANYLOXYPHENYLUREA HERBICIDES AND DICAMBA, TRICLOPYR, MECOPROP, FLUROXYPYR, BENTAZONE, OR METRIBUZIN

TECHNICAL FIELD

This invention relates to a herbicidal composition and a herbicidal method. More specifically, this invention relates to a herbicidal composition which exhibits excellent herbicidal activity even in a comparatively small dosage, and a method of controlling weeds with same.

TECHNICAL BACKGROUND

Wheat, corn, rice, soybean, etc., are important crops, and a variety of herbicides have been used to achieve an increase in yields of these crops. However, conventional herbicides are hardly satisfactory in respect of herbicidal activity and safety for crops. It is desired to develop a safe herbicide which kills detrimental weeds in a small dosage, and shows no phytotoxicity to crops.

As such a herbicide, Japanese Laid-Open (Kokai) Patent Publication No. 10779/1988 (Sho 63-10779) discloses and proposes compounds of the following formula (IA)

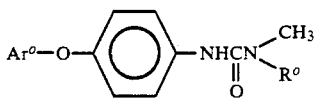

(IA)

wherein $Ar^o$ is a group of the formula,

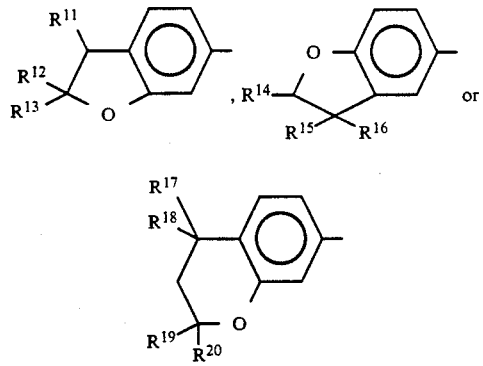

in which $R^{11}$ to $R^{13}$ and $R^{15}$ to $R^{19}$ are the same as or different from each other and each is a hydrogen atom, a methyl group or an ethyl group, and each of $R^{14}$ and $R^{20}$ is a hydrogen atom, a hydroxyl group, a methyl group, a methoxy group or an ethoxy group, and $R^o$ is a methyl group or a methoxy group.

Japanese Laid-Open (Kokai) Patent Publication No. 201180/1988 (Sho 63-201180) discloses a herbicidal composition comprising, as active ingredients, at least one compound selected from the group of urea derivative compounds of the following formula (IB)

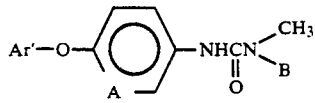

(IB)

wherein:
Ar' is a group of the formula

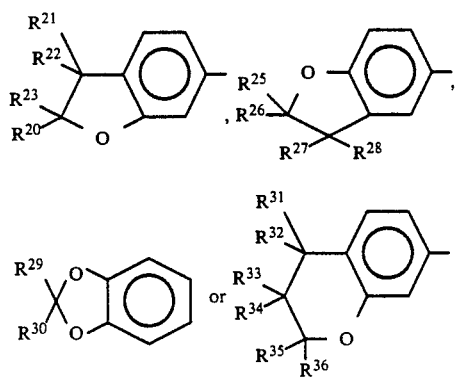

wherein $R^{21}$ to $R^{35}$ are the same as or different from each other and each is a hydrogen atom, a lower alkyl group or a lower alkoxyl group, $R^{36}$ is a hydrogen atom, a lower alkyl group, a lower alkoxy group or a hydroxyl group provided that $R^{22}$ and $R^{23}$, $R^{26}$ and $R^{27}$, $R^{29}$ and $R^{30}$, $R^{31}$ and $R^{33}$, or $R^{33}$ and $R^{35}$ may be bonded to each other to form an alkylene chain optionally substituted with a lower alkyl group and may form a 5- or 6-membered ring together with carbon atoms to which these groups are bonded, or $R^{31}$ and $R^{32}$ may be bonded to each other to form an ethylenedioxyl group, or $R^{34}$ and $R^{35}$ may be bonded to each other to form a dichloromethylene group, A is a nitrogen atom or

in which X is a hydrogen atom, a chlorine atom, a nitro group or a trifluoromethyl group, and B is a hydrogen atom, a methyl group or a methoxy group, and at least one compound selected from the group consisting of the following compounds (2A) to (2P): (2A) 4-chlorobutyn-2-yl N-(3-chlorophenyl)carbamate, (2B) 1,2-dimethyl-3,5-diphenyl-1H-pyrazolium methylsulfate, (2C) methyl 2-[4-(2,4-dichlorophenoxy)phenoxy]propionate, (2D) 3-(4-isopropylphenyl)-1,1-dimethylurea, (2E) 3-(3-chloro-4-methylphenyl)-1,1-dimethylurea, (2F) ethyl 2-[N-benzoyl-N-(3,4-dichlorophenyl)amino]propionate, (2G) S-2,3,3-trichloro-2-propenyl-N,N-diisopropylthiocarbamate, (2H) 4-hydroxy-3,5-diiodobenzonitrile, (2I) 2-chloro-N-(4-methoxy-6-methyl-1,3,5-triazin-2-ylaminocarbonyl)benzene sulfonamide, (2J) 3-(2-benzothiazolyl)-1,3-dimethylurea, (2K) 2-chloro-4-ethylamino-6-isopropylamino-1,3,5-triazine, (2L) 2-(4-chloro-6-ethylamino-1,3,5-triazin-2-yl)amino-2-methylpropionitrile, (2M) 2-(3,5-dichlorophenyl)-2-(2,2,2-trichloroethyl)oxirane, (2N) 2-chloro-2'-ethyl-N-(2-methoxy-1-methylethyl)-6'-methylacetanilide, (2O) 2-chloro-2',6'-diethyl-N-methoxymethylacetanilide, and (2P) 2-chloro-N-isopropyl-N-(3,3,5-trimethylcyclohexenyl)acetamide.

Further, the following compounds (3A) to (3P) are known to be herbicidally active compounds: (3A) 3-(5-tert-butyl-1,3,4-thiadiazolyl-2-yl)-1,3-dimethylurea, (3B) 1,3-dimethyl-3-(5-trifluoromethyl-1,3,4-thiadiazoyl-2-yl)urea, (3C) 1-(5-ethylsulfonyl-1,3,4-thiadiazoyl-2-yl)-1,3-dimethylurea, (3D) 3-(3,4-dichlorophenyl)-1,1-dimethylurea, (3E) 3-(3,4-dichlorophenyl)-1-methoxy-1-methylurea, (3F) 3,6-dichloro-2-methoxybenzoic acid, (3G) [(3,5,6-trichloro-2-pyridyl)-oxy]acetic acid triethylamine salt, (3H) 4-chloro-2-methylphenoxy acetic acid, (3I) 2-(4-chloro-2-methylphenoxy)propionic acid, (3J) 4-amino-3,5-dichloro-6-fluoro-2-pyridyloxy acetic acid, (3K) isopropyl N-(3-chlorophenyl)carbamate ester, (3L) N,N-diethylthiolcarbamic acid-S-(2-chlorobenzyl)ester, (3M) 2-methylthio-4-isopropylamino-6-methylamino-1,3,5-triazine, (3N) 2-chloro-4,6-bis(ethylamino)-1,3,5-triazine, (3O) 4-amino-6-tert-butyl-3-methylthio-1,2,4-triazin-5(4H)-one, and (3P) 3-isopropyl-1H-2,1,3-benzothiazin-4(3H)-one-2,2-dioxde.

However, the above compound (1A) and the above compounds (3A) to (3P) have drawbacks that when these compounds are used alone, they have an effect on controlling various weeds only when used in a high dosage, but use of them in a low dosage is limited to very small kind of controllable weeds. These drawbacks remain to be solved.

The above Japanese Laid-Open Patent Publication discloses the following: The composition comprising a combination of the above compound (1B) with one of the compounds (2A) to (2P) is a composition comprising a combination of the compound (1B) which is not necessarily sufficient in the herbicidal activity against gramineous weeds such as wild oat, blackgrass, etc., with one of the compounds (2A) to (2G), (2J) and (2M) to (2P) which are excellent in the herbicidal activity against these gramineous weeds, with one of the compounds (2H) and (2I) which are excellent in the herbicidal activity against broad-leaved weeds, or with one of the compounds (2K) and (2L) which are excellent in the herbicidal activity against annual broad-leaved weeds and some gramineous weeds, and the composition comprising one of the above combinations exhibits a herbicidal effect that cannot be obtained when the above compounds are used alone.

DISCLOSURE OF THE INVENTION

It is an object of this invention to provide a novel herbicidal composition comprising a novel combination of herbicidally active compounds.

It is another object of this invention to provide a herbicidal composition having excellent herbicidal activity even in a relatively small dose.

It is further another object of this invention to provide a herbicidal composition having excellent herbicidal effect and being capable of controlling weeds which are difficult to control with a herbicidally active compound alone.

It is still further another object of this invention to provide a herbicidal composition having high safety in use for narrow-leaved crops such as wheat, corn, etc., in particular.

It is yet another object of this invention to provide a method of controlling weeds, which comprises applying a novel combination of herbicidally active compounds, provided by this invention, but simultaneously and separately applying the herbicidally active compounds in an area where weeds to be controlled occur.

These and other objects and advantages of this invention will become more apparent from the following description.

According to this invention, the above objects and advantages of this invention are, in the first place, achieved by a herbicidal composition containing, as active ingredients, (A) at least one compound selected from the group consisting of compounds of the following formula (I)

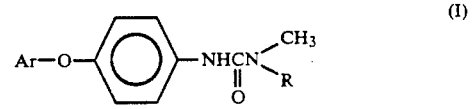

wherein:

Ar is selected from the organic groups of the following formulae (I)-a, (I)-b and (I)-c,

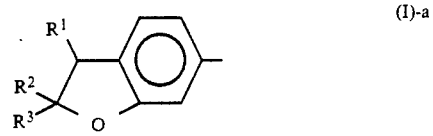

in which $R^1$ to $R^3$ are the same as or different from each other and are a hydrogen atom, a methyl group or an ethyl group,

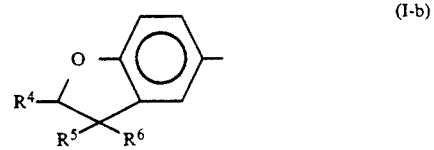

in which $R^4$ is a hydrogen atom, a hydroxyl group, a methyl group, a methoxy group or an ethoxy group, and $R^5$ and $R^6$ are the same as or different from each other and are a hydrogen atom, a methyl group or an ethyl group, and

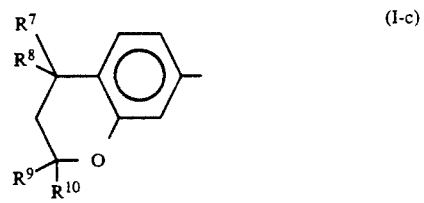

in which $R^7$ to $R^9$ are the same as or different from each other and are a hydrogen atom, a methyl group or an ethyl group, and $R^{10}$ is a hydrogen atom, a hydroxyl group, a methyl group, a methoxy group or an ethoxy group, and R is a methyl group or a methoxy group, and (B) at least one compound selected from the group consisting of compounds of the following formulae (II)-1, (II)-2, (II)-3, (II)-4, (II)-5 and (II)-6,

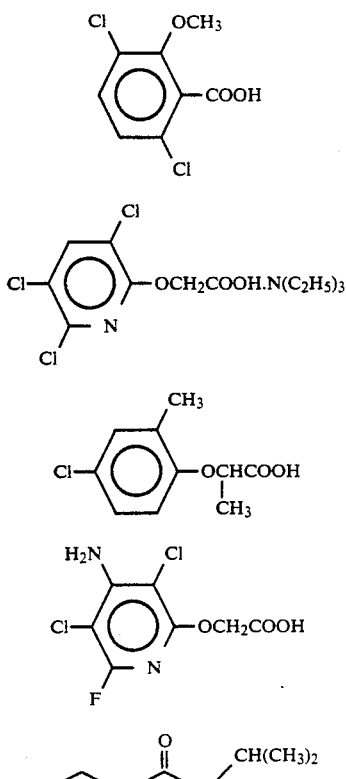

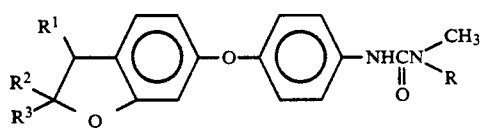

and

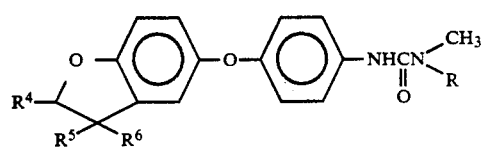

The compounds of the formula (I) wherein Ar is (I)-a, the compounds of the formula (I) wherein Ar is (I)-b and the compounds of the formula (I) wherein A is (I)-c are represented by (I)-1, (I)-2 and (I)-3, respectively.

(I)-1

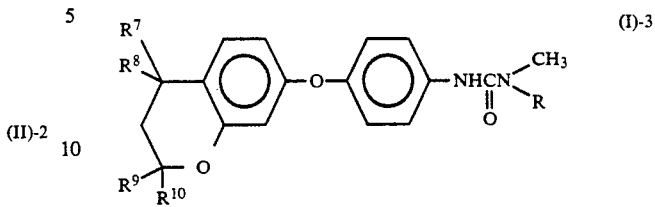

wherein $R^1$ to $R^3$ are the same as or different from each other and are a hydrogen atom, a methyl group or an ethyl group, (I)-2 wherein $R^4$ is a hydrogen atom, a hydroxyl group, a methyl group, a methoxy group or an ethoxy group, and $R^5$ and $R^6$ are the same as or different from each other and are a hydrogen atom, a methyl group or an ethyl group, and (I)-3 wherein $R^7$ to $R^9$ are the same as or different from each other and are a hydrogen atom, a methyl group or an ethyl group, and $R^{10}$ is a hydrogen atom, a hydroxyl group, a methyl group, a methoxy group or an ethoxy group.

Examples of the compounds of the above formula (I) include compounds listed in Table 1 (compounds of the formula (I)-1), compounds listed in Table 2 (compounds of the formula (I)-2) and compounds listed in Table 3 (compounds of the formula (I)-3).

TABLE 1

| Compound No. | $R^1$ | $R^2$ | $R^3$ | R |
|---|---|---|---|---|
| 1 | H | H | H | $CH_3$ |
| 2 | H | H | H | $OCH_3$ |
| 3 | $CH_3$ | H | H | $CH_3$ |
| 4 | $CH_3$ | H | H | $OCH_3$ |
| 5 | $CH_3$ | $CH_3$ | H | $CH_3$ |
| 6 | $CH_3$ | $CH_3$ | H | $OCH_3$ |
| 7 | H | $CH_3$ | $CH_3$ | $CH_3$ |
| 8 | H | $CH_3$ | $CH_3$ | $OCH_3$ |
| 9 | H | H | $C_2H_5$ | $CH_3$ |
| 10 | H | H | $C_2H_5$ | $OCH_3$ |
| 11 | H | $CH_3$ | $C_2H_5$ | $CH_3$ |
| 12 | H | $CH_3$ | $C_2H_5$ | $OCH_3$ |
| 13 | $CH_3$ | $CH_3$ | $CH_3$ | $CH_3$ |
| 14 | $CH_3$ | $CH_3$ | $CH_3$ | $OCH_3$ |
| 15 | $CH_3$ | $CH_3$ | $C_2H_5$ | $CH_3$ |
| 16 | $CH_3$ | $CH_3$ | $C_2H_5$ | $OCH_3$ |
| 17 | $C_2H_5$ | H | H | $CH_3$ |
| 18 | $C_2H_5$ | H | H | $OCH_3$ |
| 19 | H | $CH_3$ | H | $CH_3$ |
| 20 | H | $CH_3$ | H | $OCH_3$ |
| 21 | H | $C_2H_5$ | $C_2H_5$ | $CH_3$ |
| 22 | H | $C_2H_5$ | $C_2H_5$ | $OCH_3$ |
| 23 | $C_2H_5$ | $CH_3$ | $CH_3$ | $CH_3$ |
| 24 | $C_2H_5$ | $CH_3$ | $CH_3$ | $OCH_3$ |

TABLE 2

| Compound No. | $R^4$ | $R^5$ | $R^6$ | R |
|---|---|---|---|---|
| 25 | $CH_3$ | H | H | $CH_3$ |
| 26 | $CH_3$ | H | H | $OCH_3$ |
| 27 | H | $CH_3$ | H | $CH_3$ |
| 28 | H | $CH_3$ | H | $OCH_3$ |
| 29 | H | $C_2H_5$ | H | $CH_3$ |
| 30 | H | $C_2H_5$ | H | $OCH_3$ |
| 31 | $OCH_3$ | $C_2H_5$ | H | $CH_3$ |

TABLE 2-continued

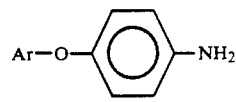

| Compound No. | R⁴ | R⁵ | R⁶ | R |
|---|---|---|---|---|
| 32 | OCH₃ | C₂H₅ | H | OCH₃ |
| 33 | CH₃ | CH₃ | H | CH₃ |
| 34 | CH₃ | CH₃ | H | OCH₃ |
| 35 | OC₂H₅ | CH₃ | H | CH₃ |
| 36 | OC₂H₅ | CH₃ | H | OCH₃ |
| 37 | OCH₃ | CH₃ | CH₃ | CH₃ |
| 38 | OCH₃ | CH₃ | CH₃ | OCH₃ |
| 39 | OCH₃ | CH₃ | C₂H₅ | CH₃ |
| 40 | OCH₃ | CH₃ | C₂H₅ | OCH₃ |
| 41 | OCH₃ | C₂H₅ | C₂H₅ | CH₃ |
| 42 | OCH₃ | C₂H₅ | C₂H₅ | OCH₃ |
| 43 | OC₂H₅ | CH₃ | CH₃ | CH₃ |
| 44 | OC₂H₅ | CH₃ | CH₃ | OCH₃ |
| 45 | H | CH₃ | CH₃ | CH₃ |
| 46 | H | CH₃ | CH₃ | OCH₃ |
| 47 | OC₂H₅ | C₂H₅ | H | CH₃ |
| 48 | OC₂H₅ | C₂H₅ | H | OCH₃ |

TABLE 3

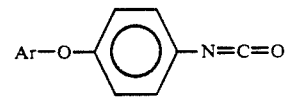

| Compound No. | R⁷ | R⁸ | R⁹ | R¹⁰ | R |
|---|---|---|---|---|---|
| 49 | H | H | H | H | CH₃ |
| 50 | H | H | H | H | OCH₃ |
| 51 | CH₃ | H | H | H | CH₃ |
| 52 | CH₃ | H | H | H | OCH₃ |
| 53 | H | H | CH₃ | H | CH₃ |
| 54 | H | H | CH₃ | H | OCH₃ |
| 55 | CH₃ | CH₃ | H | H | CH₃ |
| 56 | CH₃ | CH₃ | H | H | OCH₃ |
| 57 | H | H | CH₃ | CH₃ | CH₃ |
| 58 | H | H | CH₃ | CH₃ | OCH₃ |
| 59 | CH₃ | CH₃ | CH₃ | H | CH₃ |
| 60 | CH₃ | CH₃ | CH₃ | H | OCH₃ |
| 61 | CH₃ | H | CH₃ | CH₃ | CH₃ |
| 62 | CH₃ | H | CH₃ | CH₃ | OCH₃ |
| 63 | CH₃ | CH₃ | CH₃ | OH | CH₃ |
| 64 | CH₃ | CH₃ | CH₃ | OH | OCH₃ |
| 65 | CH₃ | CH₃ | CH₃ | OCH₃ | CH₃ |
| 66 | CH₃ | CH₃ | CH₃ | OCH₃ | OCH₃ |
| 67 | CH₃ | CH₃ | CH₃ | OC₂H₅ | CH₃ |
| 68 | CH₃ | CH₃ | CH₃ | OC₂H₅ | OCH₃ |
| 69 | H | H | C₂H₅ | H | CH₃ |
| 70 | H | H | C₂H₅ | H | OCH₃ |
| 71 | H | H | OCH₃ | H | CH₃ |
| 72 | H | H | OCH₃ | H | OCH₃ |
| 73 | H | H | OC₂H₅ | H | CH₃ |
| 74 | H | H | OC₂H₅ | H | OCH₃ |
| 75 | C₂H₅ | H | H | H | CH₃ |
| 76 | C₂H₅ | H | H | H | OCH₃ |
| 77 | CH₃ | H | CH₃ | H | CH₃ |
| 78 | CH₃ | H | CH₃ | H | OCH₃ |
| 79 | CH₃ | H | OCH₃ | H | CH₃ |
| 80 | CH₃ | H | OCH₃ | H | OCH₃ |
| 81 | CH₃ | H | OC₂H₅ | H | CH₃ |
| 82 | CH₃ | H | OC₂H₅ | H | OCH₃ |
| 83 | H | H | CH₃ | C₂H₅ | CH₃ |
| 84 | H | H | CH₃ | C₂H₅ | OCH₃ |
| 85 | H | H | CH₃ | OCH₃ | CH₃ |
| 86 | H | H | CH₃ | OCH₃ | OCH₃ |
| 87 | H | H | CH₃ | OC₂H₅ | CH₃ |
| 88 | H | H | CH₃ | OC₂H₅ | OCH₃ |

TABLE 3-continued

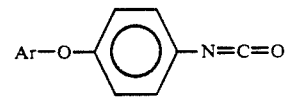

| Compound No. | R⁷ | R⁸ | R⁹ | R¹⁰ | R |
|---|---|---|---|---|---|
| 89 | H | H | C₂H₅ | OCH₃ | CH₃ |
| 90 | H | H | C₂H₅ | OCH₃ | OCH₃ |
| 91 | CH₃ | H | CH₃ | OCH₃ | CH₃ |
| 92 | CH₃ | H | CH₃ | OCH₃ | OCH₃ |
| 93 | CH₃ | H | C₂H₅ | OCH₃ | CH₃ |
| 94 | CH₃ | H | C₂H₅ | OCH₃ | OCH₃ |

The compounds of the above formula (I) can be produced by the method disclosed in Japanese Laid-Open (Kokai) Patent Publication No. 10779/1988 (Sho 63-10779), i.e. either (i) by reacting an aniline derivative of the following formula, $$Ar-O-\langle\bigcirc\rangle-NH_2$$

wherein Ar is as defined in the above formula (I), with methyl isocyanate, N,N-dimethylcarbamic acid chloride or N-methoxy-N-methylcarbamic acid chloride, or (ii) by reacting an isocyanic acid ester derivative of the following formula, $$Ar-O-\langle\bigcirc\rangle-N=C=O$$

wherein Ar is as defined in the above formula (I), with an amino acid of the following formula,

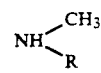

wherein R is as defined in the above formula (I).

In the composition of this invention, the herbicidally active compound(s) which are used together with the compound(s) of the above formula (I) are selected from the specified compounds of the formulae (II)-1 to (II)-6.

The compound (II)-1 is the same as the foregoing compound (3F), called dicamba, i.e. 3,6-dichloro-2-methoxybenzoic acid.

The compound (II)-2 is the same as the foregoing compound (3G), called triclopyr, i.e. [3,5,6-trichloro-2-pyridyl)-oxy]acetic acid.triethylamine salt.

The compound (II)-3 is the same as the foregoing compound (3I), called MCPP, i.e. 2-(4-chloro-2-methylphenoxy)-propionic acid.

The compound (II)-4 is the same as the foregoing compound (3J), called fluroxypyr, i.e. 4-amino-3,5-dichloro-6-fluoro-2-pyridineoxy acetic acid.

The compound (II)-5 is the same as the foregoing compound (3P), called bentazone, i.e. 3-isopropyl-1H-2,1,3-benzothiazin-4(3H)-one-2,2-dioxide.

The compound (II)-6 is the same as the foregoing compound (30), called Metribuzin, i.e. 4-amino-6-(1,1-dimethylethyl)-3-(methylthio)-1,2,4-triazin-5(4H)-one.

The herbicidal composition of this invention contains at least one compound selected from the compounds of the formula (I) and at least one compound selected from the compounds of the formulae (II)-1 to (II)-6, and optionally may further contain at least one compound selected from the foregoing compounds (2A) to (2P), (3A) to (3E), (3H) and (3K) to (3N).

The rate of application of each of the compounds of the formula (I) and the compounds of the formula (II)-1 to (II)-6 differs depending upon the types of weeds, their growth stage, their occurrence density, etc. Generally, it is preferred that in the herbicidal composition of this invention, the dose of the compound(s) of the formula (I) is 0.05 to 0.5 kg/ha, and the dose of the compound(s) of the formulae (II)-1 to (II)-6 is 0.05 to 1 kg/ha.

The herbicidal composition of this invention may be applied to weeds at various growth stages. In particular, the herbicidal composition of this invention exhibits an excellent herbicidal effect when it is applied to stalks and leaves of weeds cleaning their growing period.

The herbicides composition of this invention is preferably used and applied in the following formulations. The above active ingredients are mixed with a carrier, a surfactant, a dispersant, an adjuvant, etc., and the mixture is made, for example, into granules, a wettable powder, an emulsifiable concentrate, fine granules, a dust, etc., according to conventional methods. The carrier is preferably selected from solid carriers such as talc, bentonite, clay, kaolin, diatomaceous earth, white carbon, vermiculite, slaked lime, quartz sand, ammonium sulfate, urea, etc., and liquid carriers such as isopropyl alcohol, xylene, cyclohexanone, etc. The surfactant and dispersant are selected, for example, from a salt of alcohol sulfate ester, alkylsulfonate, lignin sulfonate, polyoxyethylene glycol ether, polyoxyethylene alkylaryl ether, polyoxyethylene sorbitan monoalkylate, etc. The adjuvant is selected, for example, from carboxymethyl cellulose, polyethylene glycol, gum arabic, etc.

The herbicidal composition of this invention may also be used, as required, upon mixing with an insecticide, a germicide or other herbicide or as a composite herbicide containing them.

The "other herbicide" above is especially preferably selected from the forgoing compounds (2A) to (2F).

In general, when the composite herbicide is prepared by incorporating other herbicide of the compounds (2A) to (2F) into a mixture composition of a compound of the formula (I) with a compound of the formulae (II)-1 to (II)-6, the amount of the compound(s) of the formulae (2A) to (2F) is preferably 0.1 to 2 kg/ha based on a mixture of 0.05 to 0.5 kg/ha of the compound(s) of the formula (I) with 0.05 to 1 kg/ha of the compound(s) of the formulae (II)-1 to (II)-6.

The herbicidal composition of this invention exhibits excellent herbicidal activity against a variety of broad-leaved weeds such as velvetleaf (*Abutilon theophrasti*), cocklebur (*Xanthium strumarium*), pigweed redroot (*Amaranthus viridis*), lambsquarters common(-*Chenopodium album*), jimson weed (*Datura stramonium*), blackjack common(*Bidens pilosa*), morningglory perennial(*Ipomoea learii*), bindweed (*Calystegia japonica*), smartweed (*Polygonum longisetum*), black nightshade (*Solanum nigrum*), violet field (*Viola arvensis*), field speedwell (*Veronica persica*), ivyleaf speedwell (*Veronica hederaefolia*), chickweed (*Stellaria media*), wild mustard (*Sinapis arvensis*), Shepherd's purse (*Capsella bursa-pastoris*), deadnettle red (*Lamium purpurem*), henbit (*Lamium amplexicaule*), chamomile (*Matricaria chamomilla*), forget-me-not field (*Myosotis arvensis*), and shows high safety for useful crops such as wheat (*Triticum aestivum*), barley (*Hordeum vulgare*), corn (*Zea mays*), etc.

The present inventors have further found that even when the herbicides constituting the herbicidal composition of this invention are simultaneously but separately applied to an area where weeds to be controlled occur thereby to realize a combination of these herbicides on the weeds or in soil in said area, the completely same effect as that of the herbicidal composition of this invention can be achieved.

According to this invention, therefore, there is provided a method of controlling weeds, which comprises applying at least one of the compounds of the formula (I) and at least one of the compounds of the formula (II)-1 to (II)-6 simultaneously as separate herbicides to an area where weeds to be controlled occur.

In the above method, the herbicide of the compound(s) of the formula (I) and the herbicide of the compound(s) of the formula (II)-1 to (II)-6 can be respectively formulated in the same manner as in the formulation of the herbicidal composition of this invention.

In the method of this invention, the compound(s) of the formula (I) and the compound(s) of the formula (II)-1 to (II)-6 may be simultaneously applied as separate herbicides or may be applied after mixing these separate herbicides before application and, as required, diluting the mixture.

EXAMPLES

The following Examples illustrate this invention further in detail.

To begin with, Formulation Examples of herbicidal compositions of this invention are described, in which "%" stands for "% by weight".

FORMULATION EXAMPLE 1

Wettable Powder

Six percent of one of the compounds of the general formula (I), 6 to 24% of one of the compounds of the general formulae (II)-1 to (II)-6, 3% of a sodium salt of higher alcohol sulfate ester and 85 to 67% of kaolin were homogeneously mixed, and the resultant mixture was pulverized to form a wettable powder.

FORMULATION EXAMPLE 2

Emulsifiable Concentrate

Ten percent of one of the compounds of the general formula (I), 10 to 40% of one of the compounds of the general formulae (II)-1 to (II)-6, 10% of polyoxyethylene alkylaryl ether, 30% of cyclohexanone and 40 to 10% of dimethylformamide were homogeneously mixed and dissolved to form an emulsifiable concentrate.

The herbicidal composition of this invention in the above formulation is applied directly or upon diluted in a suitable concentration.

EXAMPLE 1

Sieved upland farm soil (clay loam) was filled in plastic pots of 1/2,000 a, and seeds of cocklebur, velvetleaf, jimson weed, pigweed, morningglory, blackjack and corn (dent corn) were sown and covered 1 cm high with soil. These plants were grown in a greenhouse. When the corn grew to the five-leaf stage, a prescribed amout of the wettable powder which was prepared according to Formulation Example 1 was added to 1.5 liters/are of water, and the mixture was sprayed to the stalks and leaves of the weeds with a microsprayer. In this case, a 1/2,000 NEOESTERIN solution was added as a spreader. After the application of the wettable powders, the pots of the above treated weeds were allowed to stand in the greenhouse. One month after the treatment, the herbicidal compounds or compositions were evaluated on the herbicidal effects on the weeds and phytotoxicity to the corn on the basis of the following standard, and the results are shown in Table 4.

| Rating | Rating Standards Herbicidal effect | Phytotoxicity |
|---|---|---|
| 5 | withered | do |
| 4.5 | 90% to 99% | do |
| 4 | 80% to 89% | do |
| 3.5 | 70% to 79% | do |
| 3 | 60% to 69% | do |
| 2.5 | 50% to 59% | do |
| 2 | 40% to 49% | do |
| 1.5 | 30% to 39% | do |
| 1 | 20% to 29% | do |
| 0.5 | 1% to 19% | do |
| 0 | no herbicidal effect | no phytotoxicity |

Asterisks (*) in Tables 4 to 8 mean Comparative Examples in which one of the compounds of the formula (I) or one of the compounds of the formulae (II)-1 to (II)-6 was used alone.

Note to Tables 4 to 7

The alphabets in the columns of "Herbicidal effect" and "Phytotoxicity" represents the following weed and crop.
a: cocklebur
b: velvetleaf
c: jimson weed
d: pigweed
e: morningglory
f: blackjack
g: corn

TABLE 4

| Compound | Dose (kg/ha) | a | b | c | d | e | f | Phytotoxicity g |
|---|---|---|---|---|---|---|---|---|
| 14* | 0.25 | 3 | 3 | 5 | 5 | 2 | 2 | 0 |
| 14 + (II)-1 | 0.125 + 0.063 | 5 | 5 | 5 | 5 | 4 | 4 | 0 |
| (II)-1* | 0.125 | 4 | 4 | 4 | 4 | 3 | 3 | 1 |
| 14 + (II)-2 | 0.125 + 0.125 | 5 | 5 | 5 | 5 | 4 | 4 | 0 |
| (II)-2* | 0.25 | 5 | 2 | 2 | 2 | 0 | 0 | 0 |
| 15* | 0.25 | 4 | 4 | 5 | 5 | 3 | 4 | 0 |
| 15 + (II)-1 | 0.125 + 0.063 | 5 | 5 | 5 | 5 | 5 | 5 | 0 |
| 15 + (II)-2 | 0.125 + 0.125 | 5 | 5 | 5 | 5 | 5 | 5 | 0 |
| 38* | 0.25 | 4 | 4 | 5 | 5 | 4 | 4 | 0 |
| 38 + (II)-1 | 0.125 + 0.063 | 5 | 5 | 5 | 5 | 5 | 5 | 0 |
| 38 + (II)-2 | 0.125 + 0.125 | 5 | 5 | 5 | 5 | 5 | 5 | 0 |
| 44* | 0.25 | 4 | 4 | 5 | 5 | 4 | 4 | 0 |
| 44 + (II)-1 | 0.125 + 0.063 | 5 | 5 | 5 | 5 | 5 | 5 | 0 |
| 44 + (II)-2 | 0.125 + 0.125 | 5 | 5 | 5 | 5 | 5 | 5 | 0 |
| 54* | 0.25 | 4 | 4 | 5 | 5 | 3 | 3 | 0 |
| 54 + (II)-1 | 0.125 + 0.063 | 5 | 5 | 5 | 5 | 4 | 4 | 0 |
| 54 + (II)-2 | 0.125 + 0.125 | 5 | 5 | 5 | 5 | 4 | 5 | 0 |
| 57* | 0.25 | 4 | 4 | 5 | 5 | 4 | 4 | 0 |
| 57 + (II)-1 | 0.125 + 0.063 | 5 | 5 | 5 | 5 | 5 | 5 | 0 |
| 57 + (II)-2 | 0.125 + 0.125 | 5 | 5 | 5 | 5 | 5 | 5 | 0 |
| 64* | 0.25 | 4 | 5 | 5 | 5 | 4 | 4 | 0 |
| 64 + (II)-1 | 0.125 + 0.063 | 5 | 5 | 5 | 5 | 5 | 5 | 0 |
| 64 + (II)-2 | 0.125 + 0.125 | 5 | 5 | 5 | 5 | 5 | 5 | 0 |
| 66* | 0.25 | 4 | 5 | 5 | 5 | 4 | 4 | 0 |
| 66 + (II)-1 | 0.125 + 0.063 | 5 | 5 | 5 | 5 | 5 | 5 | 0 |
| 66 + (II)-2 | 0.125 + 0.125 | 5 | 5 | 5 | 5 | 5 | 5 | 0 |

EXAMPLE 2

Example 1 was repeated for evaluation of herbicidal effects and phytotoxicity except that the herbicidally active compounds were changed. The same rating standard as that in Example 1 was used. Table 5 shows the results.

TABLE 5

| Compound | Dose (kg/ha) | a | b | c | d | e | f | Phytotoxicity g |
|---|---|---|---|---|---|---|---|---|
| 13* | 0.25 | 3 | 4 | 4 | 5 | 2 | 3 | 0 |
| 13 + (II)-3 | 0.125 + 0.125 | 5 | 5 | 5 | 5 | 5 | 5 | 0 |
| 13 + (II)-4 | 0.125 + 0.125 | 5 | 5 | 5 | 5 | 5 | 5 | 0 |
| 5* | 0.25 | 3 | 3 | 3 | 5 | 3 | 2 | 0 |
| 5 + (II)-3 | 0.125 + 0.125 | 4 | 4 | 4 | 5 | 5 | 5 | 0 |
| 5 + (II)-4 | 0.125 + 0.125 | 5 | 5 | 5 | 5 | 5 | 5 | 0 |
| 22* | 0.25 | 3 | 4 | 4 | 4 | 4 | 3 | 0 |
| 22 + (II)-3 | 0.125 + 0.125 | 4 | 5 | 4 | 5 | 5 | 4 | 0 |
| 22 + (II)-4 | 0.125 + 0.125 | 4 | 5 | 4 | 5 | 5 | 4 | 0 |
| 31* | 0.25 | 4 | 4 | 4 | 5 | 4 | 3 | 0 |
| 31 + (II)-3 | 0.125 + 0.125 | 5 | 4 | 5 | 5 | 5 | 5 | 0 |
| 31 + (II)-4 | 0.125 + 0.125 | 5 | 5 | 5 | 5 | 5 | 5 | 0 |
| 37* | 0.25 | 3 | 4 | 4 | 5 | 4 | 3 | 0 |
| 37 + (II)-3 | 0.125 + 0.125 | 4 | 4 | 5 | 5 | 5 | 4 | 0 |
| 37 + (II)-4 | 0.125 + 0.125 | 5 | 5 | 5 | 5 | 5 | 5 | 0 |
| 41* | 0.25 | 4 | 4 | 5 | 4 | 5 | 4 | 0 |
| 41 + (II)-3 | 0.125 + 0.125 | 5 | 5 | 5 | 5 | 5 | 5 | 0 |
| 41 + (II)-4 | 0.125 + 0.125 | 5 | 5 | 5 | 5 | 5 | 5 | 0 |
| 49* | 0.25 | 3 | 3 | 4 | 4 | 4 | 4 | 0 |
| 49 + (II)-3 | 0.125 + 0.125 | 4 | 4 | 5 | 5 | 5 | 5 | 0 |
| 49 + (II)-4 | 0.125 + 0.125 | 5 | 5 | 5 | 5 | 5 | 5 | 0 |
| 49 + (II)-5 | 0.125 + 0.125 | 5 | 5 | 5 | 5 | 5 | 5 | 0 |
| 66* | 0.25 | 4 | 5 | 5 | 5 | 5 | 4 | 0 |
| 66 + (II)-3 | 0.125 + 0.125 | 5 | 5 | 5 | 5 | 5 | 5 | 0 |
| 66 + (II)-4 | 0.125 + 0.125 | 5 | 5 | 5 | 5 | 5 | 5 | 0 |
| 66 + (II)-5 | 0.125 + 0.125 | 5 | 5 | 5 | 5 | 5 | 5 | 0 |
| 79* | 0.25 | 3 | 4 | 4 | 5 | 4 | 3 | 0 |
| 79 + (II)-3 | 0.125 + 0.125 | 4 | 5 | 5 | 5 | 5 | 5 | 0 |
| 79 + (II)-4 | 0.125 + 0.125 | 5 | 5 | 5 | 5 | 5 | 5 | 0 |
| 79 + (II)-5 | 0.125 + 0.125 | 5 | 5 | 5 | 5 | 5 | 5 | 0 |
| 64* | 0.25 | 3 | 4 | 4 | 5 | 4 | 3 | 0 |
| 64 + (II)-3 | 0.125 + 0.125 | 4 | 5 | 5 | 5 | 5 | 4 | 0 |
| 64 + (II)-4 | 0.125 + 0.125 | 5 | 5 | 5 | 5 | 5 | 5 | 0 |
| 64 + (II)-5 | 0.125 + 0.125 | 5 | 4 | 5 | 5 | 4 | 4 | 0 |

EXAMPLE 3

Example 1 was repeated for evaluation of herbicidal effects and phytotoxicity except that Formulation Example 2 was used in place of Formulation Example 1. The same rating standard as that in Example 1 was used. Table 6 shows the results.

TABLE 6

| Compound | Dose (kg/ha) | a | b | c | d | e | f | Phytotoxicity g |
|---|---|---|---|---|---|---|---|---|
| 1* | 0.25 | 3 | 3 | 3 | 3 | 2 | 4 | 0 |
| 1 + (II)-1 | 0.125 + 0.125 | 5 | 5 | 5 | 5 | 4 | 5 | 0 |
| 1 + (II)-4 | 0.125 + 0.125 | 5 | 5 | 5 | 5 | 5 | 5 | 0 |
| 1 + (II)-5 | 0.125 + 0.125 | 5 | 5 | 5 | 5 | 5 | 5 | 0 |
| 1 + (II)-6 | 0.125 + 0.125 | 5 | 5 | 5 | 5 | 5 | 5 | 0 |
| 15* | 0.25 | 3 | 3 | 3 | 4 | 3 | 3 | 0 |

(TABLE 4-continued)

| Compound | Dose (kg/ha) | a | b | c | d | e | f | Phytotoxicity g |
|---|---|---|---|---|---|---|---|---|
| 64 + (II)-1 | 0.125 + 0.063 | 5 | 5 | 5 | 5 | 5 | 5 | 0 |
| 64 + (II)-2 | 0.125 + 0.125 | 5 | 5 | 5 | 5 | 5 | 5 | 0 |
| 66* | 0.25 | 4 | 5 | 5 | 5 | 4 | 4 | 0 |
| 66 + (II)-1 | 0.125 + 0.063 | 5 | 5 | 5 | 5 | 5 | 5 | 0 |
| 66 + (II)-2 | 0.125 + 0.125 | 5 | 5 | 5 | 5 | 5 | 5 | 0 |

TABLE 6-continued

| Compound | Dose (kg/ha) | Herbicidal effect | | | | | | Phytotoxicity |
|---|---|---|---|---|---|---|---|---|
| | | a | b | c | d | e | f | g |
| 15 + (II)-1 | 0.125 + 0.125 | 5 | 5 | 5 | 5 | 4 | 5 | 0 |
| 15 + (II)-4 | 0.125 + 0.125 | 4 | 5 | 5 | 5 | 5 | 5 | 0 |
| 15 + (II)-5 | 0.125 + 0.125 | 4 | 5 | 5 | 5 | 5 | 5 | 0 |
| 15 + (II)-6 | 0.125 + 0.125 | 5 | 5 | 5 | 5 | 5 | 5 | 0 |
| 34* | 0.25 | 3 | 4 | 5 | 5 | 3 | 4 | 0 |
| 34 + (II)-1 | 0.125 + 0.125 | 5 | 5 | 5 | 5 | 5 | 5 | 0 |
| 34 + (II)-4 | 0.125 + 0.125 | 5 | 5 | 5 | 5 | 5 | 5 | 0 |
| 34 + (II)-5 | 0.125 + 0.125 | 4 | 5 | 5 | 5 | 5 | 5 | 0 |
| 34 + (II)-6 | 0.125 + 0.125 | 5 | 5 | 5 | 5 | 5 | 5 | 0 |
| 57* | 0.25 | 3 | 3 | 4 | 4 | 3 | 3 | 0 |
| 57 + (II)-1 | 0.125 + 0.125 | 5 | 5 | 5 | 5 | 4 | 5 | 0 |
| 57 + (II)-4 | 0.125 + 0.125 | 5 | 5 | 5 | 5 | 4 | 5 | 0 |
| 57 + (II)-5 | 0.125 + 0.125 | 5 | 5 | 5 | 5 | 5 | 5 | 0 |
| 57 + (II)-6 | 0.125 + 0.125 | 5 | 5 | 5 | 5 | 5 | 5 | 0 |
| 66* | 0.25 | 3 | 4 | 5 | 5 | 4 | 5 | 0 |
| 66 + (II)-1 | 0.125 + 0.125 | 5 | 5 | 5 | 5 | 5 | 5 | 0 |
| 66 + (II)-4 | 0.125 + 0.125 | 5 | 5 | 5 | 5 | 5 | 5 | 0 |
| 66 + (II)-5 | 0.125 + 0.125 | 5 | 5 | 5 | 5 | 4 | 5 | 0 |
| 66 + (II)-6 | 0.125 + 0.125 | 5 | 5 | 5 | 5 | 5 | 5 | 0 |
| 79* | 0.25 | 4 | 3 | 5 | 5 | 3 | 4 | 0 |
| 79 + (II)-1 | 0.125 + 0.125 | 5 | 5 | 5 | 5 | 4 | 5 | 0 |
| 79 + (II)-4 | 0.125 + 0.125 | 5 | 5 | 5 | 5 | 5 | 5 | 0 |
| 79 + (II)-5 | 0.125 + 0.125 | 4 | 5 | 5 | 5 | 4 | 5 | 0 |
| 79 + (II)-6 | 0.125 + 0.125 | 5 | 5 | 5 | 5 | 5 | 5 | 0 |
| 92* | 0.25 | 4 | 4 | 5 | 5 | 3 | 4 | 0 |
| 92 + (II)-1 | 0.125 + 0.125 | 5 | 5 | 5 | 5 | 4 | 5 | 0 |
| 92 + (II)-4 | 0.125 + 0.125 | 5 | 5 | 5 | 5 | 4 | 5 | 0 |
| 92 + (II)-5 | 0.125 + 0.125 | 5 | 5 | 5 | 5 | 4 | 5 | 0 |
| 92 + (II)-6 | 0.125 + 0.125 | 5 | 5 | 5 | 5 | 5 | 5 | 0 |

EXAMPLE 4

Six percent of one of the compounds of the general formula (I), 3% of a sodium salt of higher alcohol sulfate ester and 91% of kaolin were homogeneously mixed, and the mixture was pulverized to form a wettable powder. Separately, 6 to 24% of one of the compounds of the general formulae (II)-1 to (II)-6, 3% of a sodium salt of higher alcohol sulfate ester and 73 to 91% of kaolin were homogeneously mixed, and the mixture was pulverized to form a wettable powder. A prescribed amount of the above wettable powder of the compound of the general formula (I) and a presecribed amount of the above wettable powder of the compound of the general formulae (II)-1 to (II)-6 were added to 1.5 liters/are of water to dilute a mixture, and the resultant mixture was sprayed to stalks and leaves with a microsprayer.

The plants and rating standard for evaluation of herbicidal effect and phytotoxicity were the same as those in Example 1. Table 7 shows the results.

TABLE 7

| Compound | Dose (kg/ha) | Herbicidal effect | | | | | | Phytotoxicity |
|---|---|---|---|---|---|---|---|---|
| | | a | b | c | d | e | f | g |
| 5* | 0.25 | 3 | 3 | 3 | 5 | 3 | 2 | 0 |
| 5 + (II)-1 | 0.125 + 0.125 | 4 | 4 | 5 | 5 | 4 | 4 | 0 |

TABLE 7-continued

| Compound | Dose (kg/ha) | Herbicidal effect | | | | | | Phytotoxicity |
|---|---|---|---|---|---|---|---|---|
| | | a | b | c | d | e | f | g |
| 5 + (II)-3 | 0.125 + 0.125 | 4 | 5 | 5 | 5 | 4 | 4 | 0 |
| 5 + (II)-5 | 0.125 + 0.125 | 4 | 5 | 5 | 5 | 4 | 3 | 0 |
| 5 + (II)-6 | 0.125 + 0.125 | 5 | 5 | 5 | 5 | 5 | 5 | 0 |
| 35* | 0.25 | 3 | 3 | 4 | 4 | 3 | 3 | 0 |
| 35 + (II)-1 | 0.125 + 0.125 | 5 | 5 | 5 | 5 | 4 | 4 | 0 |
| 35 + (II)-3 | 0.125 + 0.125 | 5 | 5 | 5 | 5 | 5 | 4 | 0 |
| 35 + (II)-5 | 0.125 + 0.125 | 5 | 5 | 5 | 5 | 4 | 4 | 0 |
| 35 + (II)-6 | 0.125 + 0.125 | 5 | 5 | 5 | 5 | 5 | 5 | 0 |
| 48* | 0.25 | 4 | 4 | 4 | 5 | 3 | 4 | 0 |
| 48 + (II)-1 | 0.125 + 0.125 | 5 | 5 | 5 | 5 | 5 | 5 | 0 |
| 48 + (II)-2 | 0.125 + 0.125 | 5 | 5 | 5 | 5 | 5 | 5 | 0 |
| 48 + (II)-3 | 0.125 + 0.125 | 5 | 5 | 5 | 5 | 4 | 4 | 0 |
| 48 + (II)-6 | 0.125 + 0.125 | 5 | 5 | 5 | 5 | 5 | 5 | 0 |
| 65* | 0.25 | 3 | 4 | 5 | 5 | 4 | 3 | 0 |
| 65 + (II)-1 | 0.125 + 0.125 | 5 | 5 | 5 | 5 | 5 | 5 | 0 |
| 65 + (II)-2 | 0.125 + 0.125 | 5 | 5 | 5 | 5 | 5 | 5 | 0 |
| 65 + (II)-3 | 0.125 + 0.125 | 5 | 5 | 5 | 5 | 5 | 4 | 0 |
| 65 + (II)-4 | 0.125 + 0.125 | 5 | 5 | 5 | 5 | 5 | 5 | 0 |
| 66* | 0.25 | 4 | 4 | 5 | 5 | 5 | 4 | 0 |
| 66 + (II)-1 | 0.125 + 0.125 | 5 | 5 | 5 | 5 | 5 | 5 | 0 |
| 66 + (II)-4 | 0.125 + 0.125 | 5 | 5 | 5 | 5 | 5 | 5 | 0 |
| 66 + (II)-5 | 0.125 + 0.125 | 5 | 5 | 5 | 5 | 5 | 5 | 0 |
| 66 + (II)-6 | 0.125 + 0.125 | 5 | 5 | 5 | 5 | 5 | 5 | 0 |

EXAMPLE 5

Six percent of one of the compounds of the general formula (I), 6% of one of the compounds of the general formulae (II)-1 to (II)-6, 6% of one of the compounds (2A) to (2F), 3% of a sodium salt of higher alcohol sulfate ester and 79% of kaolin were homogeneously mixed, and the mixture was pulverized to form a wettable powder.

The wettable powder was diluted with 1.5 liters/are of water, and the resultant dilute solution was sprayed to stalks and leaves with a microsprayer.

The plants used were winter wheat (*Triticum aestrivum*), catchweed (*Galium aparine*), chickweed (*Stellaria media*), violet field (*Viola arvensis*), field speedwell (*Veronica persica*), henbit (*Lamium amplexicaule*), chamomile (*Matricaria chamomilla*) and blackgrass (*Alopecurus myosuroides*), and the rating standard for herbicial effect and phytotoxicity were the same as that used in Example 1. Table 8 shows the results.

Note to Table 8

The alphabets in the columns of "Herbicidal effect" and "Phytotoxicity" represent the following weed and crop.

h: catchweed
i: chickweed
j: violet field
k: field speedwell
l: henbit
m: chamomile
n: blackgrass
o: winter wheat

TABLE 8

| Compound | Dose (kg/ha) | Herbicidal effect | | | | | | Phytotoxicity |
|---|---|---|---|---|---|---|---|---|
| | | h | i | j | k | l | m | n | o |
| 35* | 0.25 | 1 | 4 | 3 | 5 | 4 | 2 | 0 | 0 |
| 35 + (II)-1 + 2A | 0.125 + 0.125 + 0.5 | 4 | 5 | 4 | 5 | 5 | 3 | 4 | 0 |
| 35 + (II)-3 + 2B | 0.125 + 0.125 + 0.5 | 4 | 5 | 4 | 5 | 5 | 3 | 3 | 0 |
| 35 + (II)-3 + 2C | 0.125 + 0.125 + 0.5 | 3 | 5 | 4 | 5 | 5 | 3 | 5 | 0 |
| 35 + (II)-3 + 2D | 0.125 + 0.125 + 0.5 | 3 | 5 | 5 | 5 | 5 | 5 | 5 | 0 |
| 35 + (II)-3 + 2E | 0.125 + 0.125 + 0.5 | 3 | 5 | 4 | 5 | 5 | 5 | 5 | 0 |
| 35 + (II)-3 + 2F | 0.125 + 0.125 + 0.5 | 3 | 5 | 4 | 5 | 5 | 4 | 3 | 0 |
| 35 + (II)-4 + 2A | 0.125 + 0.125 + 0.5 | 5 | 5 | 4 | 5 | 5 | 4 | 3 | 0 |

TABLE 8-continued

| Compound | Dose (kg/ha) | Herbicidal effect | | | | | | | Phytotoxicity |
|---|---|---|---|---|---|---|---|---|---|
| | | h | i | j | k | l | m | n | o |
| 35 + (II)-4 + 2B | 0.125 + 0.125 + 0.5 | 5 | 5 | 5 | 5 | 5 | 4 | 3 | 0 |
| 35 + (II)-4 + 2C | 0.125 + 0.125 + 0.5 | 5 | 5 | 5 | 5 | 5 | 4 | 5 | 0 |
| 35 + (II)-4 + 2D | 0.125 + 0.125 + 0.5 | 5 | 5 | 5 | 5 | 5 | 5 | 5 | 0 |
| 35 + (II)-4 + 2E | 0.125 + 0.125 + 0.5 | 5 | 5 | 5 | 5 | 5 | 5 | 5 | 0 |
| 35 + (II)-4 + 2F | 0.125 + 0.125 + 0.5 | 5 | 5 | 4 | 5 | 5 | 4 | 4 | 0 |
| 43* | 0.25 | 1 | 4 | 2 | 5 | 5 | 1 | 0 | 0 |
| 43 + (II)-1 + 2D | 0.125 + 0.125 + 0.5 | 4 | 5 | 4 | 5 | 5 | 5 | 5 | 0 |
| 43 + (II)-1 + 2E | 0.125 + 0.125 + 0.5 | 3 | 5 | 5 | 5 | 5 | 5 | 5 | 0 |
| 43 + (II)-3 + 2D | 0.125 + 0.125 + 0.5 | 3 | 5 | 4 | 5 | 5 | 5 | 5 | 0 |
| 43 + (II)-3 + 2E | 0.125 + 0.125 + 0.5 | 3 | 5 | 5 | 5 | 5 | 5 | 5 | 0 |
| 43 + (II)-4 + 2C | 0.125 + 0.125 + 0.5 | 5 | 5 | 4 | 5 | 5 | 5 | 5 | 0 |
| 43 + (II)-4 + 2D | 0.125 + 0.125 + 0.5 | 5 | 5 | 3 | 5 | 5 | 5 | 5 | 0 |
| 43 + (II)-4 + 2E | 0.125 + 0.125 + 0.5 | 5 | 5 | 4 | 5 | 5 | 5 | 5 | 0 |
| 43 + (II)-5 + 2C | 0.125 + 0.125 + 0.5 | 3 | 5 | 4 | 5 | 5 | 5 | 5 | 0 |
| 43 + (II)-5 + 2D | 0.125 + 0.125 + 0.5 | 3 | 5 | 4 | 5 | 5 | 5 | 5 | 0 |
| 43 + (II)-5 + 2E | 0.125 + 0.125 + 0.5 | 3 | 5 | 4 | 5 | 5 | 5 | 5 | 0 |
| 66* | 0.25 | 2 | 5 | 4 | 5 | 5 | 3 | 1 | 0 |
| 66 + (II)-1 + 2C | 0.125 + 0.125 + 0.5 | 4 | 5 | 4 | 5 | 5 | 3 | 5 | 0 |
| 66 + (II)-1 + 2D | 0.125 + 0.125 + 0.5 | 4 | 5 | 4 | 5 | 5 | 5 | 5 | 0 |
| 66 + (II)-1 + 2E | 0.125 + 0.125 + 0.5 | 4 | 5 | 4 | 5 | 5 | 5 | 5 | 0 |
| 66 + (II)-2 + 2C | 0.125 + 0.125 + 0.5 | 4 | 5 | 4 | 5 | 5 | 4 | 5 | 0 |
| 66 + (II)-2 + 2D | 0.125 + 0.125 + 0.5 | 4 | 5 | 4 | 5 | 5 | 5 | 5 | 0 |
| 66 + (II)-2 + 2E | 0.125 + 0.125 + 0.5 | 4 | 5 | 4 | 5 | 5 | 5 | 5 | 0 |
| 66 + (II)-3 + 2C | 0.125 + 0.125 + 0.5 | 4 | 5 | 4 | 5 | 5 | 4 | 5 | 0 |
| 66 + (II)-3 + 2D | 0.125 + 0.125 + 0.5 | 4 | 5 | 4 | 5 | 5 | 5 | 5 | 0 |
| 66 + (II)-3 + 2E | 0.125 + 0.125 + 0.5 | 4 | 5 | 4 | 5 | 5 | 5 | 5 | 0 |
| 66 + (II)-4 + 2C | 0.125 + 0.125 + 0.5 | 5 | 5 | 5 | 5 | 5 | 4 | 5 | 0 |
| 66 + (II)-4 + 2D | 0.125 + 0.125 + 0.5 | 5 | 5 | 5 | 5 | 5 | 5 | 5 | 0 |
| 66 + (II)-4 + 2E | 0.125 + 0.125 + 0.5 | 5 | 5 | 5 | 5 | 5 | 5 | 5 | 0 |
| 66 + (II)-5 + 2C | 0.125 + 0.125 + 0.5 | 3 | 5 | 4 | 5 | 5 | 4 | 5 | 0 |
| 66 + (II)-5 + 2D | 0.125 + 0.125 + 0.5 | 3 | 5 | 4 | 5 | 5 | 5 | 5 | 0 |
| 66 + (II)-5 + 2E | 0.125 + 0.125 + 0.5 | 3 | 5 | 4 | 5 | 5 | 5 | 5 | 0 |
| 66 + (II)-6 + 2C | 0.125 + 0.125 + 0.5 | 3 | 5 | 5 | 5 | 5 | 5 | 5 | 0 |
| 66 + (II)-6 + 2D | 0.125 + 0.125 + 0.5 | 3 | 5 | 4 | 5 | 5 | 5 | 5 | 0 |
| 66 + (II)-6 + 2E | 0.125 + 0.125 + 0.5 | 3 | 5 | 5 | 5 | 5 | 5 | 5 | 0 |
| 80* | 0.25 | 0 | 5 | 3 | 5 | 4 | 2 | 1 | 0 |
| 80 + (II)-4 + 2A | 0.125 + 0.125 + 0.5 | 5 | 5 | 5 | 5 | 5 | 3 | 3 | 0 |
| 80 + (II)-4 + 2B | 0.125 + 0.125 + 0.5 | 5 | 5 | 5 | 5 | 5 | 3 | 3 | 0 |
| 80 + (II)-4 + 2C | 0.125 + 0.125 + 0.5 | 5 | 5 | 5 | 5 | 5 | 3 | 5 | 0 |
| 80 + (II)-4 + 2D | 0.125 + 0.125 + 0.5 | 5 | 5 | 5 | 5 | 5 | 5 | 5 | 0 |
| 80 + (II)-4 + 2E | 0.125 + 0.125 + 0.5 | 5 | 5 | 5 | 5 | 5 | 5 | 5 | 0 |
| 80 + (II)-4 + 2F | 0.125 + 0.125 + 0.5 | 5 | 5 | 5 | 5 | 5 | 4 | 4 | 0 |
| 80 + (II)-5 + 2A | 0.125 + 0.125 + 0.5 | 5 | 5 | 5 | 5 | 5 | 4 | 3 | 0 |
| 80 + (II)-5 + 2B | 0.125 + 0.125 + 0.5 | 5 | 5 | 5 | 5 | 5 | 4 | 4 | 0 |
| 80 + (II)-5 + 2C | 0.125 + 0.125 + 0.5 | 5 | 5 | 5 | 5 | 5 | 4 | 4 | 0 |
| 80 + (II)-5 + 2D | 0.125 + 0.125 + 0.5 | 5 | 5 | 5 | 5 | 5 | 5 | 5 | 0 |
| 80 + (II)-5 + 2E | 0.125 + 0.125 + 0.5 | 5 | 5 | 5 | 5 | 5 | 5 | 5 | 0 |
| 80 + (II)-5 + 2F | 0.125 + 0.125 + 0.5 | 5 | 5 | 5 | 5 | 5 | 4 | 4 | 0 |
| 80 + (II)-6 + 2A | 0.125 + 0.125 + 0.5 | 5 | 5 | 5 | 5 | 5 | 5 | 5 | 0 |
| 80 + (II)-6 + 2B | 0.125 + 0.125 + 0.5 | 5 | 5 | 5 | 5 | 5 | 5 | 5 | 0 |
| 80 + (II)-6 + 2C | 0.125 + 0.125 + 0.5 | 5 | 5 | 5 | 5 | 5 | 5 | 5 | 0 |
| 80 + (II)-6 + 2D | 0.125 + 0.125 + 0.5 | 5 | 5 | 5 | 5 | 5 | 5 | 5 | 0 |
| 80 + (II)-6 + 2E | 0.125 + 0.125 + 0.5 | 5 | 5 | 5 | 5 | 5 | 5 | 5 | 0 |
| 80 + (II)-6 + 2F | 0.125 + 0.125 + 0.5 | 5 | 5 | 5 | 5 | 5 | 5 | 5 | 0 |

We claim:

1. A herbicidal composition containing, as active ingredients,
(A) at least one compound selected from the group consisting of compounds of the following formula (I)

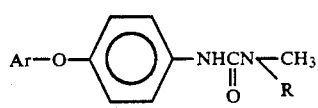

(I)

wherein:
Ar is selected from the organic groups of the following formulae (I)-a, (I)-b and (I)-c,

(I)-a in which $R^1$ to $R^3$ are the same as or different from each other and are a hydrogen atom, a methyl group or an ethyl group,

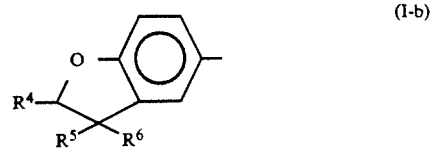

(I-b)

in which $R^4$ is a hydrogen atom, a hydroxyl group, a methyl group, a methoxy group or an ethoxy group, and $R^5$ and $R^6$ are the same as or different from each other and are a hydrogen atom, a methyl group or an ethyl group,

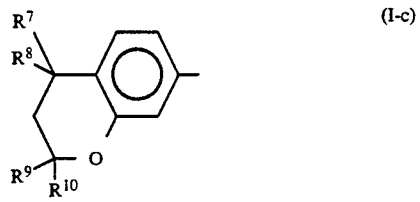
(I-c)

in which $R^7$ to $R^9$ are the same as or different from each other and are a hydrogen atom, a methyl group or an ethyl group, and $R^{10}$ is a hydrogen atom, a hydroxyl group, a methyl group, a methoxy group or an ethoxy group, and R is a methyl group or a methoxy group, and (B) at least one compound selected from the group consisting of compounds of the following formulae (II)-1, (II)-2, (II)-3, (II)-4, (II)-5 and (II)-6.

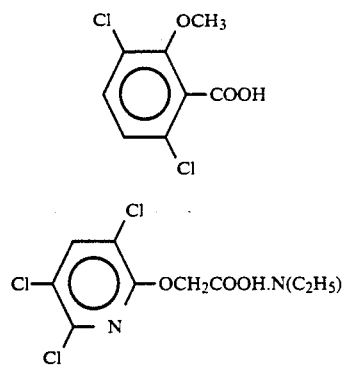
(II)-1

(II)-2

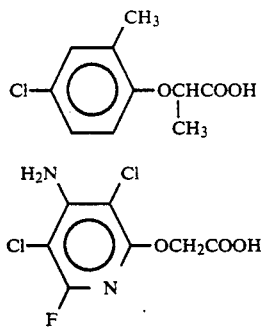
(II)-3

(II)-4

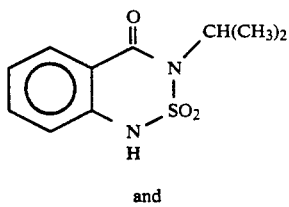
(II)-5 and

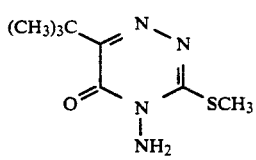
(II)-6

2. A herbicidal composition set forth in claim 1, which further contains at least one compound selected from the group consisting of 4-chlorobutyn-2-yl N-(3-chlorophenyl)carbamate, 1,2-dimethyl-3,5-diphenyl-1H-pyrazolium methylsulfate, methyl 2-[4-(2,4-dichlorophenoxy)phenoxy]propionate, 3-(4-isopropylphenyl)-1,1-dimethylurea, 3-(3-chloro-4-methylphenyl)-1,1-dimethylurea, ethyl 2-[N-benzoyl-N-(3,4-dichlorophenyl)amino]propionate, S-2,3,3-trichloro-2-propenyl-N,N-diisopropylthiocarbamate, 4-hydroxy-3,5-diiodobenzonitrile, 2-chloro-N-(4-methoxy-6-methyl-1,3,5-triazin-2-ylaminocarbonyl)benzene sulfonamide, 3-(2-benzothiazolyl)-1,3-dimethylurea, 2-chloro-4-ethylamino-6-isopropylamino-1,3,5-triazine, 2-(4-chloro-6-ethylamino-1,3,5-triazin-2-yl)amino-2-methylpropionitrile, 2-(3,5-dichlorophenyl)-2-(2,2,2-trichloroethyl)oxirane, 2-chloro-2'-ethyl-N-(2-methoxy-1-methylethyl)-6'-methylacetanilide, 2-chloro-2',6'-diethyl-N-methoxymethyl-acetanilide, 2-chloro-N-isopropyl-N-(3,3,5-trimethylcyclohexenyl)-acetamide, 3-(5-tert-butyl-1,3,4-thiadiazolyl-2-yl)-1,3-dimethylurea, 1,3-dimethyl-3-(5-trifluoromethyl-1,3,4-thiadiazoyl-2-yl)urea, 1-(5-ethylsulfonyl-1,3,4-thiadiazoyl-2-yl)-1,3-dimethylurea, 3-(3,4-dichlorophenyl)-1,1-dimethylurea, 3-(3,4-dichlorophenyl)-1-methoxy-1-methylurea, 4-chloro-2-methylphenoxy acetate, isopropyl N-(3-chlorophenyl)-carbamate ester, N,N-diethylthiolcarbamic acid-S-(2-chlorobenzyl)ester, 2-methylthio-4-isopropylamino-6-methylamino-1,3,5-triazine and 2-chloro-4,6-bis(ethylamino)-1,3,5-triazine.

3. A method of controlling weeds, which comprises applying a herbicidally effective amount of at least one of the compounds of the following formula

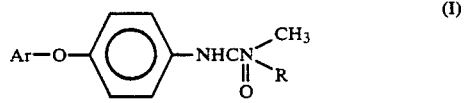
(I)

and a herbicidally effective amount of at least one of the compounds of the following formulae (II)-1 to (II)-6

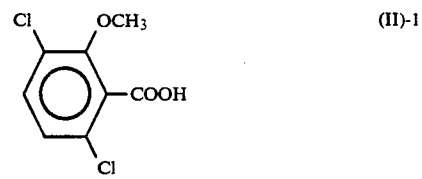
(II)-1

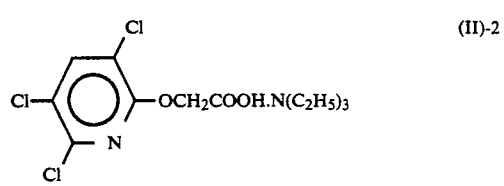
(II)-2

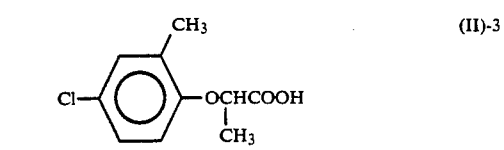
(II)-3

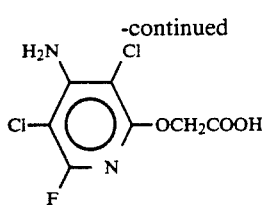

(II)-4

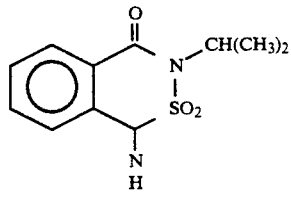

(II)-5 and

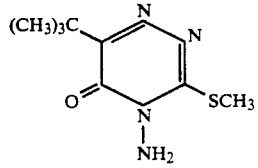

(II)-6 simultaneously as separate herbicides directly on the stalks or leaves of weeds to be controlled during growth or to the soil in an area where weeds to be controlled occur.

4. The method of controlling weeds according to claim 3 wherein an amount of at least one compound of formula I of from about 0.05 to 0.5 kg/ha and an amount of at least one compound of formula II of from about 0.05 to 1 kg/ha are applied to said area.

5. The herbicidal composition of claim 1 further comprising at least one component selected from the group consisting of a carrier, a surfactant, a dispersant, and an adjuvant.

6. The herbicidal composition of claim 1 further comprising a compound selected from the group consisting of an insecticide, a germicide and another herbicide.

7. The herbicidal composition of claim 1 which further comprises another herbicide selected from the group consisting of compounds (2A) through (2F):

(2A) 4-chlorobutyn-2-yl N-(3-chlorophenyl) carbamate, (2B) 1,2-dimethyl-3,5-diphenyl-1 H-pyrazolium methyl sulfate, (2C) methyl 2-[4-(2,4-dichlorophenoxy)-phenoxy] propionate, (2D) 3-(4-isopropylphenyl)-1,1-dimethylurea, (2E) 3-(3-chloro-4-methylphenyl)-1,1-dimethylurea and (2F) ethyl 2-[N-benzoyl-N-(3-4-dichlorophenyl amino] propionate.

8. The composition of claim 1 which comprises a wettable powder comprising about 6% by weight of a compound of the general formula (I) and from about 6 to about 24% by weight of a compound of the general formulae (II)-1 to (II)-6.

9. The composition of claim 1 which comprises an emulsifiable concentrate comprising about 10% by weight of a compound of the general formula (I) and from about 10 to 40% by weight of a compound of the general formula (II)-1 to (II)-6.

10. The composition of claim 1 which comprises as an active ingredient (A) a compound of the following formula

11. The composition of claim 1 which comprises as active ingredients compound (A) having the formula

and compound (B) having the formula (II)-1.

12. The composition of claim 1 which comprises as an active ingredient (A) a compound of the following formula

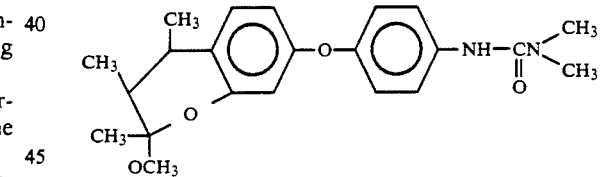

and (B) a compound of the following formula

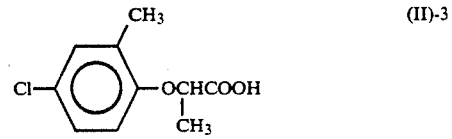

(II)-3

* * * * *